United States Patent
Chen et al.

(10) Patent No.: US 10,416,064 B2
(45) Date of Patent: Sep. 17, 2019

(54) METHODS AND SYSTEMS FOR DETERMINING GAS PERMEABILITY OF A SUBSURFACE FORMATION

(71) Applicant: Saudi Arabian Oil Company, Dharan (SA)

(72) Inventors: Huangye Chen, Cypress, TX (US); Hui-Hai Liu, Katy, TX (US); Jilin Jay Zhang, Cypress, TX (US)

(73) Assignee: Saudi Arabian Oil Company, Dhahran (SA)

(*) Notice: Subject to any disclaimer, the term of this patent is extended or adjusted under 35 U.S.C. 154(b) by 0 days.

(21) Appl. No.: 16/381,310

(22) Filed: Apr. 11, 2019

(65) Prior Publication Data

US 2019/0234859 A1    Aug. 1, 2019

Related U.S. Application Data

(63) Continuation-in-part of application No. 15/378,305, filed on Dec. 14, 2016.
(Continued)

(51) Int. Cl.
*E21B 49/02* (2006.01)
*G01N 15/08* (2006.01)

(52) U.S. Cl.
CPC ......... *G01N 15/0826* (2013.01); *E21B 49/02* (2013.01)

(58) Field of Classification Search
CPC ........... G01N 15/0826; G01N 15/0806; G01N 15/08; G01N 33/24; G01N 33/241; E21B 49/02
See application file for complete search history.

(56) References Cited

U.S. PATENT DOCUMENTS

| 4,253,327 A | 3/1981 | Wiley |
| 4,996,872 A | 3/1991 | Mueller et al. |

(Continued)

FOREIGN PATENT DOCUMENTS

| CN | 204177799 U | 2/2015 |
| WO | WO2014123966 A1 | 8/2014 |

OTHER PUBLICATIONS

Civan et al., Rigorous Modeling for Data Analysis Towards Accurate Determination of Shale Gas-Permeability by Multiple-Repeated Pressure-Pulse Transmission Tests on Crushed Samples, Oct. 27-29, 2014, SPE Annual Technical Conference and Exhibition, Amsterdam, Netherlands, 28 pp. (Year: 2014).*

(Continued)

*Primary Examiner* — Toan M Le
(74) *Attorney, Agent, or Firm* — Bracewell LLP; Constance G. Rhebergen; Vivek P. Shankam

(57) ABSTRACT

Methods and systems disclosed here include conducting two pressure-dependent permeability tests having the same range of effective stress but two different values of pore pressure. For the test with the higher pore pressure, the permeability is only impacted by the mechanical deformation of the rock, while for the one with lower pore pressure the permeability is impacted by both mechanical deformation of the rock and the Knudsen diffusion. By using the same range of effective stress, the contribution from the mechanical deformation of the rock should be the same. Therefore, by subtracting the permeability with higher pore pressure from the one with lower pore pressure, the impact of Knudsen diffusion and the mechanical deformation of the rock can be determined.

15 Claims, 13 Drawing Sheets

Related U.S. Application Data

(60) Provisional application No. 62/267,091, filed on Dec. 14, 2015.

(56) References Cited

U.S. PATENT DOCUMENTS

| | | | |
|---|---|---|---|
| 5,297,420 | A | 3/1994 | Gilliland et al. |
| 5,731,511 | A | 3/1998 | Roque et al. |
| 6,591,661 | B2 | 7/2003 | Davey |
| 7,131,317 | B2 | 11/2006 | Roland et al. |
| 2015/0354352 | A1 | 12/2015 | Moustafa et al. |
| 2017/0167964 | A1 | 6/2017 | Liu et al. |

OTHER PUBLICATIONS

Alnoaimi, K. R. et al.:"Experimental and numerical analysis of gas transport in shale including the role of sorption." SPE Annual Technical Conference and Exhibition. Society of Petroleum Engineers, 2013; pp. 1-16.

Alnoaimi, K.R. et al.; "Characterization and Measurement of Multi-Scale Gas Transport in Shale Core Samples" URTeC: 1920820, Unconventional Resources Technology Conference Aug. 25-27, 2014; pp. 1-19.

Civan, F. et al.: "Comparison of Shale Permeability to Gas Determined by Pressure-Pulse Transmission Testing of Core Plugs and Crushed Samples" SPE-178571-MS/URTeC:2154049, Unconventional Resources Technology Conference TX, USA Jul. 20-22, 2015 (13 pgs).

Civan, F. et al.: "Determining shale permeability to gas by simultaneous analysis of various pressure tests." SPE 144253; SPE Unconventional Gas Conference, Journal 17.03 (2012); pp. 717-726.

Clarkson, C.R. et al.; "Use of Pressure- and Rate-Transient Techniquest for Analyzing Core Permeability Tests for Unconventional Reservoirs" SPE 154815, Americas Unconventional Resources Conference Jun. 5-7, 2012; pp. 1-22.

Darabi, et al.: "Gas flow in ultra-tight shale strata." Journal of Fluid Mechanics 710.1 (2012): pp. 641-658.

Heller, Rob et al.; "Experimental investigation of matrix permeability of gas shales" AAPG Bulletin, V. 98, No. 5 (May 2014); pp. 975-995.

International Search Report and Written Opinion for PCT/US2016/066591; International Filing Date Dec. 14, 2016; Report dated Feb. 16, 2017 (pp. 1-14).

Jones, S. C. "A technique for faster pulse-decay permeability measurements in tight rocks." SPE 28450; SPE Annual Technical Conference & Exhibition (1994); pp. 19-26.

Liu, Hui-Hai et al.; "An Innovative Laboratory Method to Measure Pore-Pressure-Dependent Gas Permeability of Shale: Theory and Numerical Experiments" SPE 191123, SPE Reservoir Evaluation & Engineering, 2018; pp. 1-10.

\* cited by examiner

METHODS AND SYSTEMS FOR DETERMINING GAS PERMEABILITY OF A SUBSURFACE FORMATION

CROSS-REFERENCE TO RELATED PATENT APPLICATIONS

This application is a Continuation-In-Part of U.S. Non-Provisional application Ser. No. 15/378,305, filed Dec. 14, 2016, and titled "METHODS AND SYSTEMS FOR DETERMINING PORE PRESSURE-DEPENDENT GAS PERMEABILITY OF A SUBSURFACE FORMATION," which claims priority from U.S. Provisional Application No. 62/267,091, filed Dec. 14, 2015, and titled "METHODS AND SYSTEMS FOR DETERMINING PORE PRESSURE-DEPENDENT GAS PERMEABILITY OF A SUBSURFACE FORMATION," the entire contents of which are incorporated by reference.

TECHNICAL FIELD

Example embodiments relate to methods and systems for determining permeability and porosity of a subsurface rock formation using pore gas pressure.

BACKGROUND

Unlike conventional reservoirs, pores in shale formations are extremely small, typically on the order of nanometers. In these nano pores, a non-negligible portion of gas molecules collides more often with the pore wall than with other molecules, and thus so-called "slip flow" and Knudsen diffusion occur. Previous studies on gas flow in shale matrix found that the gas permeability in shale is a function of the pore gas pressure because the slip flow and Knudsen diffusion effect becomes significant when the pore gas pressure is relatively low (for example thousand pounds per square inch or lower).

Shale gas permeability as a function of pore gas pressure, resulting from "slip flow" and diffusion processes, is critical for characterizing and modeling gas flow in a shale gas reservoir. However, this important pore gas pressure-dependency is hardly considered in practice because of the lack of a practical and efficient technique that can be used routinely for determining the pressure-dependent shale gas permeability.

Pressure dependence has a significant impact on predicted gas-production rate. There are currently two approaches to measure the pressure dependence of gas permeability in the laboratory. The first one is to simply perform a number of pulse-decay permeability tests under different gas pressures. Then, these tests will provide gas permeability values for a number of gas pressures. Initially, the system is in equilibrium with a given gas pressure. A small pressure pulse is then introduced into the upstream gas reservoir such that the pulse does not have a significant disturbance to the gas pressure in the system. The pressures at the two gas reservoirs are monitored as a function of time. The pressure evolution results are fitted using analytical solutions with permeability being a fitting parameter. However, it generally takes a relatively long time to equilibrate the test system from one test pressure to the next one.

The other approach to determine the pressure dependence is to first develop a formulation of gas permeability as a function of gas pressure and then estimate values for parameters in the formulation by numerically matching the relevant test results under different gas pressure conditions. Test results are generally different from pulse-decay tests in which the pressure pulse is not limited to a small one because numerical model is flexible enough to incorporate the pulse disturbance to the system. However, non-uniqueness of parameter estimation is always a problem for inverse modeling. Also, the accuracy of estimated results from this approach is ultimately determined by that of the used formulation of gas permeability as a function of gas pressure that is not fully established yet.

SUMMARY

Example embodiments disclosed provide a method for measuring a relationship between shale gas permeability and pore gas pressure. The development is based on an analytical solution to one-dimensional gas flow under certain boundary and initial conditions. The advantages of the disclosed approach over the currently available ones include that it directly measures the relationship using a single test run and without any presumption regarding the form of parametric relationship between gas permeability and pressure. In addition, the current approach allows for estimating both shale permeability and porosity at the same time from the related measurements. In addition, the disclosed embodiments consider the impact of mechanical deformation of the rock sample. Therefore, the disclosed methods and systems include a workflow using two-or-more-step permeability tests, which can measure the impacts of Knudsen diffusion and the mechanical deformation of the rock on permeability, respectively.

One example embodiment is a transient flow method for determining permeability of a subsurface formation. The method includes extracting a sample of the subsurface formation, and positioning the sample in a pressure vessel comprising a type of natural or man-made gas or liquid and a pressure gauge. The method further includes running a first test by measuring a first pore gas pressure, $p_i$, or the initial pore gas pressure of the sample inside the pressure vessel. The method further includes applying a second pore gas pressure, $p_o$, to the inlet of the sample within pressure vessel, the second pore gas pressure being greater than the first pore gas pressure ($p_o > p_i$). The method further includes measuring a third pore gas pressure, p, at a plurality of locations as a function of time t along the sample in the pressure vessel. The method also includes determining a total gas mass per unit volume of the subsurface formation, m, and, determining the permeability function, k(p), of the subsurface formation from gas transport parameter D(p), based at least in part on the first pore gas pressure, the second pressure, the third pore gas pressure as a function of time, and the gas density, with a single test run. The method may also include determining the gas transport parameter of the subsurface formation, D(p), using a first formula:

$$D(p) = -\frac{\int_{p_i}^{p} \frac{\lambda}{2} \frac{dm}{dp} dp}{\frac{dp}{d\lambda}}$$

where $p_i$ is the first pore gas pressure inside the sample before the second pore gas pressure $p_o$ is applied, p is the third pore gas pressure at location x at time t, m is the gas density or total gas mass per unit volume of the subsurface formation, and $\lambda$ is an independent variable calculated using the formula $xt^{-1/2}$.

The method may also include determining the total gas mass per unit volume of the subsurface formation, m, using a second formula:

$$m = \phi\rho + (1-\phi)\rho_a$$

where $\phi$ is porosity of the subsurface formation, $\rho$ is gas density of the free gas, and $\rho_a$ is adsorbed gas mass per unit volume of the subsurface formation.

The method may also include determining the porosity $\phi$ of the subsurface formation using a third formula:

$$\phi = \frac{B - A\int_{p_i}^{p_0} \lambda \frac{d\rho_a}{dp} dp}{A\int_{p_i}^{p_0} \lambda \frac{d(\rho - \rho_a)}{dp} dp}$$

where A is a cross-sectional area of the sample, and B is a slope of a curve of the cumulative gas flow into the sample at x=0 (sample inlet) versus $t^{1/2}$.

The method may also include determining the slope of the curve, B, using a fourth formula:

$$B = A\int_{p_i}^{p_0} \lambda \frac{dm}{dp} dp$$

The method further includes running a second test with a fourth pressure and a fifth pressure, wherein the fourth pressure is greater than the first pressure, and the fifth pressure is greater than the second pressure. The method also includes generating a graph plotting permeability vs. effective stress for the first test and the second test. The method further includes determining impact of mechanical deformation of rock on permeability as a function of the effective stress. The method also includes determining the difference between permeability values obtained from the first test and the second test with respect to the effective stress. The method also includes determining impact of Knudsen diffusion on permeability as a function of the pore pressure.

Another example embodiment is a non-transitory computer-readable medium having computer executable instructions that cause a computer to perform the operations of reading a measurement of a first pore gas pressure, $p_i$, of a sample inside a pressure vessel. The operations further include reading a measurement of a second pore gas pressure, $p_o$, applied to the inlet of the sample, the second pore gas pressure being greater than the first pore gas pressure. The operations further include reading a measurement of a third pore gas pressure, p, as a function of time t, at a plurality of locations along the length of the sample. The operations further include determining a total gas mass per unit volume of the subsurface formation, m, and determining a permeability of the subsurface formation, k, based at least in part on the first pore gas pressure, the third pore gas pressure, and the gas density.

The computer executable instructions further cause the computer to perform the operation of determining the transport parameter of the subsurface formation D(p) using a first formula:

$$D(p) = -\frac{\int_{p_i}^{p} \frac{\lambda}{2} \frac{dm}{dp} dp}{\frac{dp}{d\lambda}}$$

where $p_i$ is the first pore gas pressure inside the pressure vessel before the second pore gas pressure $p_o$ is applied, p is the third pore gas pressure at location x at time t, m is the total gas mass per unit volume of the subsurface formation, and $\lambda$ is an independent variable calculated using the formula $xt^{-1/2}$.

The computer executable instructions further cause the computer to perform the operation of determining the total gas mass per unit volume of the subsurface formation, m, using a second formula:

$$m = \phi\rho + (1-\phi)\rho_a$$

where $\phi$ is porosity of the subsurface formation, $\rho$ is gas density of the free gas, and $\rho_a$ is adsorbed gas mass per unit volume of the subsurface formation.

The computer executable instructions further cause the computer to perform the operation of determining the porosity $\phi$ of the subsurface formation using a third formula:

$$\phi = \frac{B - A\int_{p_i}^{p_0} \lambda \frac{d\rho_a}{dp} dp}{A\int_{p_i}^{p_0} \lambda \frac{d(\rho - \rho_a)}{dp} dp}$$

where A is a cross-sectional area of the sample, and B is a slope of a curve of the cumulative gas flow into the sample at x=0 (the sample inlet) versus $t^{1/2}$.

The computer executable instructions further cause the computer to perform the operation of determining the slope of the curve, B, using a fourth formula:

$$B = A\int_{p_i}^{p_0} \lambda \frac{dm}{dp} dp$$

The operations may further include running a second test with a fourth pressure and a fifth pressure, wherein the fourth pressure is greater than the first pressure, and the fifth pressure is greater than the second pressure. The operations may also include generating a graph plotting permeability versus effective stress for the first test and the second test. The operations may further include determining impact of mechanical deformation of rock on permeability as a function of the effective stress. The operations may also include determining the difference between permeability values obtained from the first test and the second test with respect to the effective stress. The operations may also include determining impact of Knudsen diffusion on permeability as a function of the pore pressure.

DETAILED DESCRIPTION

Example methods and systems include conducting two pressure-dependent permeability tests having the same range of effective stress (which equals to confining stress minus pore pressure) but two different values of pore pressure. For the test with the higher pore pressure, the permeability is only impacted by the mechanical deformation of the rock, while for the one with lower pore pressure the permeability is impacted by both mechanical deformation of the rock and the Knudsen diffusion. By using the same range of effective stress, the contribution from the mechanical deformation of the rock should be the same. Therefore, by subtracting the permeability with higher pore pressure from the one with lower pore pressure, the impact of Knudsen diffusion and the mechanical deformation of the rock can be determined.

Figure 1:
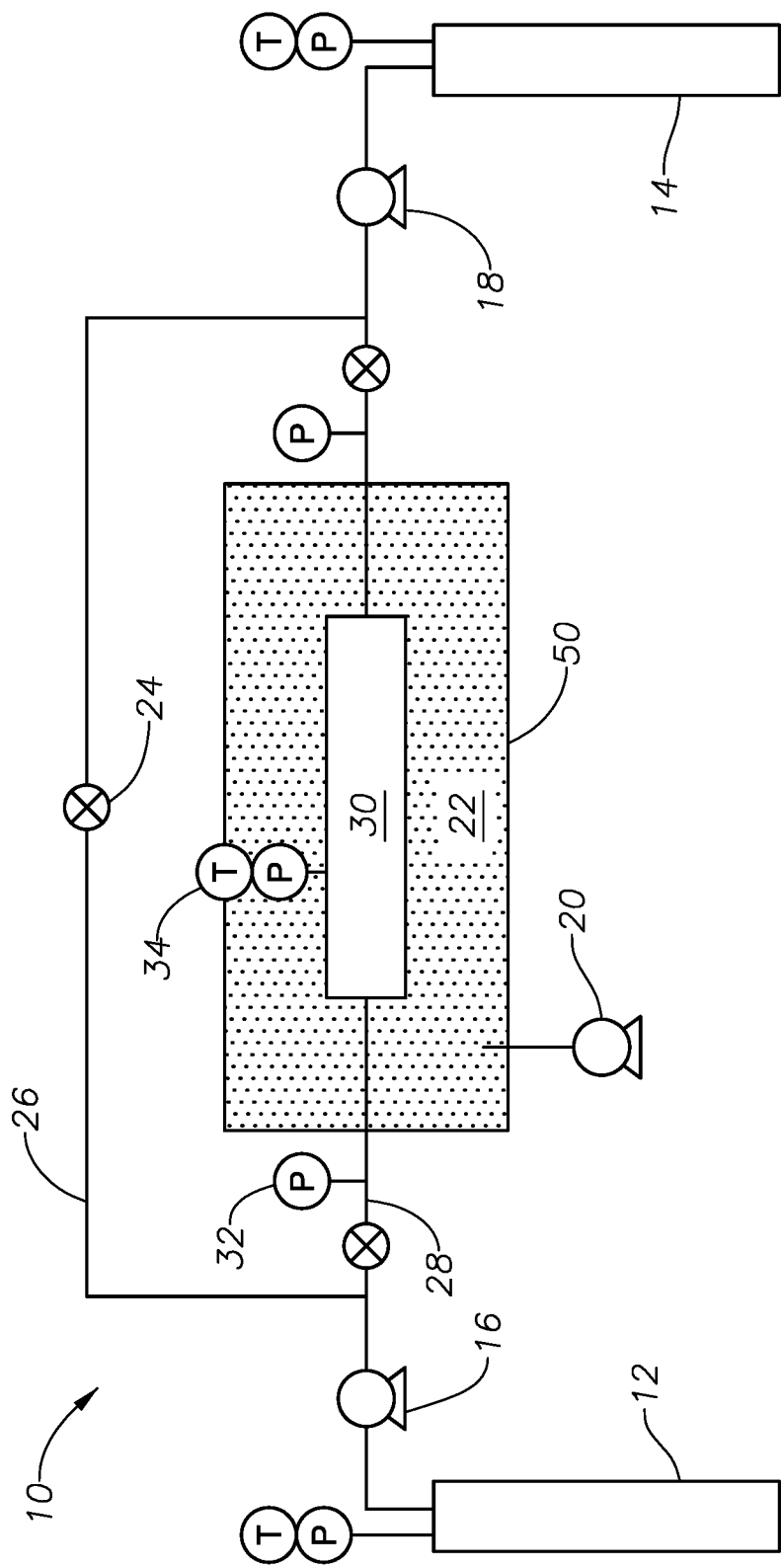
FIG. 1 illustrates an example system for determining permeability and porosity of a subsurface formation, according to one example embodiment of the disclosure.

Turning now to the figures, FIG. 1 illustrates an example system 10 for determining permeability function k(p) and porosity of a subsurface formation, according to some example embodiments of the disclosure. System 10 includes sample 30, such as a shale sample, a limestone sample, or a sandstone sample, in the form of a cylinder or column that may be extracted from the subsurface for determining characteristics of the formation. The sample 30 is placed in a pressure vessel 50 that may contain a confining fluid 22, such as gas, a water-based fluid, or an oil-based fluid. The pressure vessel 50 is coupled to pumps 16, 18 through pressure lines 28, and provides the confining pressure to the sample 30.

System 10 includes an inlet pump 16 configured to pump fluid from a first gas tank 12 into sample 30. The system also includes an outlet pump 18 configured to pump fluid from a second gas tank 14 into sample 30. Both pumps may include one or more pressure and flowrate sensors to measure and control the pressure inside the core sample assembly. Pressure vessel 50 may be equipped with a hydraulic pump 20 that may pump the confining fluid 22 into pressure vessel 50. The pressure vessel 50 may include an apparatus that monitors and regulates the pressure within the pressure vessel 50. Temperature gauge 34 and pressure gauge 32 are coupled to rock sample, and a pressure gauge 32 is coupled to the inlet of the core sample 30, respectively. Both gauges may include high accuracy transducers (with a typical accuracy of 0.01%) to measure temperature and pressure, respectively, in real-time. Inlet 28 to the core sample assembly may be diverted at a plurality of points using bypass valves 24 and an outlet pipe 26 in order to regulate the pore gas pressure (for example, the establishment of the initial pore pressure) in sample 30 which is placed in the pressure vessel 50.

Figure 2A:
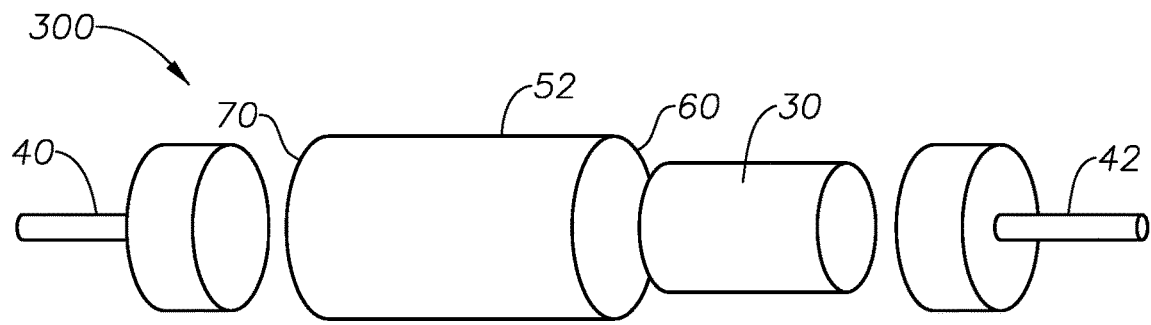
FIGS. 2A-2D illustrate an example apparatus for determining permeability and porosity of a subsurface formation, according to one example embodiment of the disclosure.
Figure 2B:
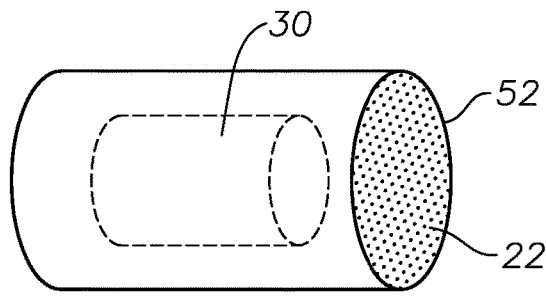
Figure 2C:
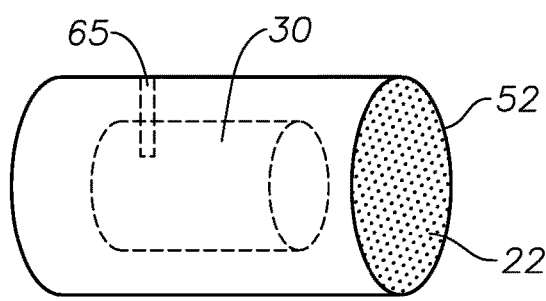

FIGS. 2A-2D illustrate in further detail an example set up for arranging a shale sample assembly 300 in the pressure vessel 50. As illustrated in FIG. 2A, the shale sample 30 is first inserted into a sleeve 52 having a length, a diameter, a first open end 60, and a second open end 70. The shale sample may be enclosed in the sleeve 52 using a first end piece or outlet 42 adapted to be inserted into the first open end 60, and a second end piece or inlet 40 adapted to be inserted into the second open end 70 of the sleeve 52. FIG. 2B illustrates the first step where the shale sample 30 is inserted into a sleeve 52. As illustrated in FIG. 2C, a through hole or a port for pressure measurement 65 is formed through the body of the sleeve 52 and into the body of the sample 30 so as to insert a tubing, such as a tubing 44 (shown in FIG. 2D). A half sleeve 46 may be disposed on the tubular sleeve 52, and the half sleeve 46 may include a second hole corresponding to the first hole 65 on the first sleeve. The tubing 44 may be coupled to a temperature gauge 34 and a pressure gauge 32 as illustrated in FIG. 1, for example. An anchoring device 48 may be used for securing the tubing 44 to the half sleeve 46, thereby forming an assembly. Other fastening devices, such as ring clamps, may be used to secure the half sleeve 46 and the sleeve 52. The inlet 40 and outlet 42 on the sample assembly 300 may be coupled through couplings on the wall or the end caps of the pressure vessel 50 to the pressure lines (such as 28), which may be coupled to the inlet pump 16 and outlet pump 18.

Figure 2D:
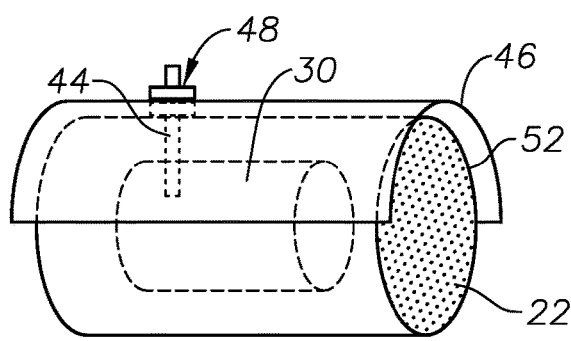
Figure 3:
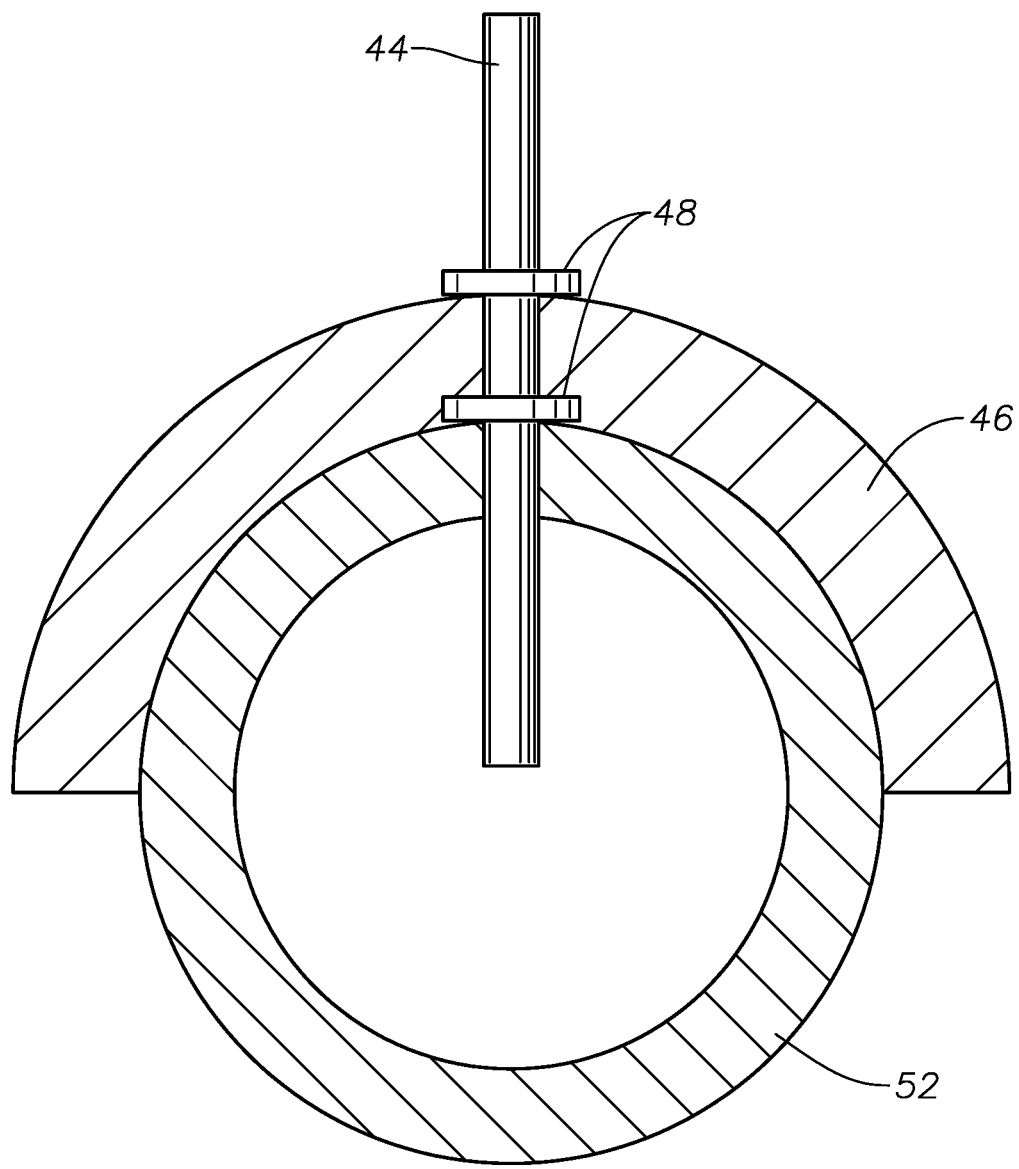
FIG. 3 illustrates an example apparatus for determining permeability and porosity of a subsurface formation, according to one example embodiment of the disclosure.

FIG. 3 illustrates a cross-sectional view of the apparatus in FIG. 2D where tubing 44, which in some embodiments may comprise steel, is inserted through the half sleeve 46, sleeve 52, and secured using anchoring devices 48. According to one example embodiment, sleeve 52 and half sleeve 46 may include at least one of rubber and a polymeric material. According to another example embodiment, an inner diameter of the half sleeve 46 may be smaller than the outer diameter of the sleeve 52. According to another example embodiment, a length of the half sleeve 46 is equal to or less than the length of the sleeve 52.

Figure 4A:
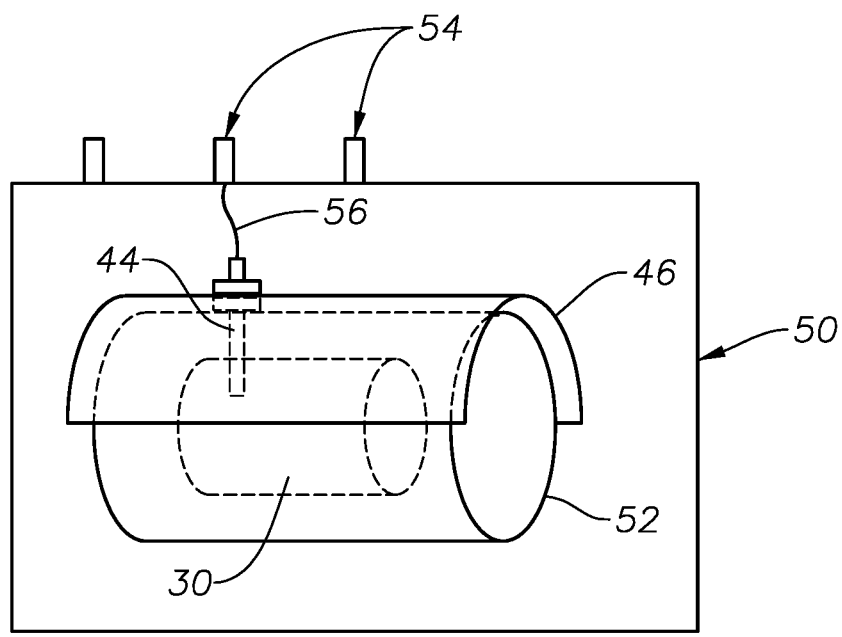
FIGS. 4A and 4B illustrate example apparatuses for determining permeability and porosity of a subsurface formation, according to some example embodiments of the disclosure.
Figure 4B:
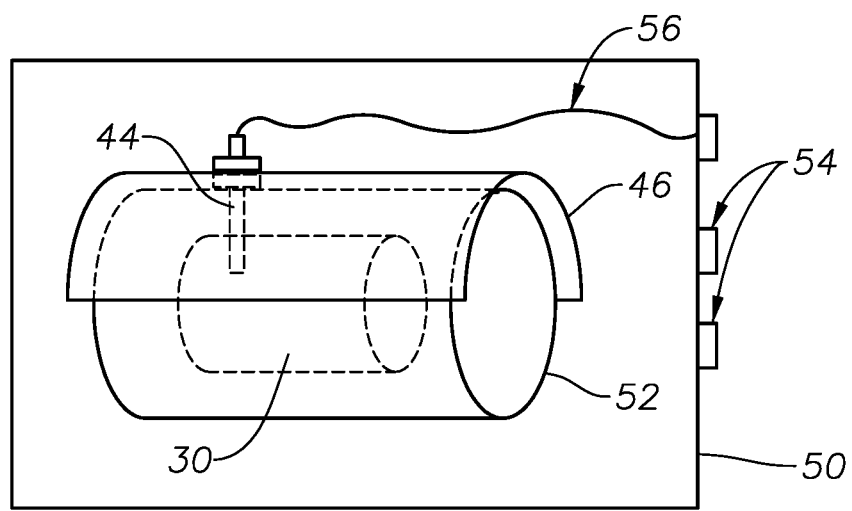

After the sleeve 52 is secured for preventing leakage from the port of pressure measurement 65, the assembly is disposed in the pressure vessel 50, as illustrated in FIG. 4A, for example. The pressure vessel 50 may include a plurality of pressure taps 54, each of which to be coupled a pressure measurement location along the rock sample. FIG. 4B illustrates an alternative arrangement where the pressure taps 54 may be configured along one end of the pressure vessel 50. In this case, multiple measurement locations along the rock sample may be instrumented according to the procedure described in FIGS. 2A-D and 3. According to one example embodiment, one or more temperature gauges 34 and pressure gauges 32 may be coupled to tubing 44 using a flexible line 56.

Analytical Method for Determining Permeability and Porosity of a Subsurface Formation The following sections provide an example method for determining permeability, k, and porosity of a subsurface formation using the system 10 illustrated in FIG. 1. The method is based on an analytical solution to one-dimensional gas flow under certain boundary and initial conditions. The governing mass balance equation for gas flow may be given by Equation 1 as follows:

$$\frac{\partial m}{\partial t} = \frac{\partial}{\partial x}\left(\frac{k\rho}{\mu}\frac{\partial p}{\partial x}\right) \quad (1)$$

where t is time, x is the spatial coordinate (a distance from the inlet of the sample along its axis), k is the permeability, $\mu$, $\rho$, and p are gas viscosity, density and pressure, respectively, (note k, $\mu$, $\rho$, are functions of p), and m is the total gas mass per unit volume of the porous medium or apparent gas density, which may be given by Equation 2 as follows:

$$m = \phi\rho + (1-\phi)\rho_a \quad (2)$$

where $\phi$ is porosity and $\rho_a$ is adsorbed gas mass per unit volume of solid phase or the subsurface formation. For conservative gases, the second term on the right hand of Equation 2 can be considered to be zero.

In Equation 1, the storage term can be rewritten as:

$$\frac{\partial m}{\partial t} = \frac{dm}{dp}\frac{\partial p}{\partial t} \quad (3)$$

The present method may relate to isothermal conditions, and therefore m may be considered a function of pressure only. Accordingly, the contributions of gas density change in pressure to storage can be given by Equation 4 as follows:

$$\frac{dm}{dp} = \phi\frac{d\rho}{dp} + (1-\phi)\frac{d\rho_a}{dp} \quad (4)$$

Taking into consideration an infinite long shale sample in the form of a cylinder/column with gas flow from the inlet (x=0) and subject to the following boundary and initial conditions:

$$p(x,t)=p_i \ (x \geq 0, t=0)$$

$$p(x,t)=p_0 \ (x=0, t>0)$$

$$p(x,t)=p_i \ (x \to \infty, t>0) \quad (5)$$

where $p_i$ is the initial pressure inside the measurement system before the elevated upstream pressure, $p_0$, is applied.

Using the transformation $$\lambda = xt^{-1/2} \quad (6)$$

Equations 5 and 1 can be transformed as follows:

$$p(\lambda)=p_i \ (\lambda \to \infty)$$

$$p(\lambda)=p_0 \ (\lambda=0) \quad (7)$$

and $$-\frac{\lambda}{2}\frac{dm}{dp}\frac{dp}{d\lambda} = \frac{d}{d\lambda}\left[D(p)\frac{dp}{d\lambda}\right] \quad (8)$$

where $$D(p) = \frac{k\rho}{\mu} \quad (9)$$

Equation 8 is an ordinary differential equation with $\lambda$ as the only independent variable.

Directly integrating Equation 8 for the interval ($\lambda$, $\infty$) yields $$D(p) = -\frac{\int_{p_i}^{p}\frac{\lambda}{2}\frac{dm}{dp}dp}{\frac{dp}{d\lambda}} \quad (10)$$

which indicates that D(p) can be fully determined when p($\lambda$) is known.

Based on the gas mass balance, the cumulative gas flow into the column (at x=0) can be determined using Equation 11 as follows:

$$M(t) = \quad (11)$$

$$A\int_0^\infty (m-m_i)dx = A(m-m_i)x\big|_0^\infty - A\int_{p_0}^{p_i} x\frac{dm}{dp}dp = A\int_{p_i}^{p_0} x\frac{dm}{dp}dp$$

where A is the cross-sectional area of the shale column. Combining Equations 11 and 6 gives $$M(t) = \left(A\int_{p_i}^{p_0}\lambda\frac{dm}{dp}dp\right)t^{\frac{1}{2}} = Bt^{\frac{1}{2}} \quad (12)$$

where B is a slope for the curve of M(t) versus $t^{1/2}$.

Combining Equations 4 and 12 gives $$\phi = \frac{B - A \int_{p_i}^{p_0} \lambda \frac{d\rho_a}{dp} dp}{A \int_{p_i}^{p_0} \lambda \frac{d(\rho - \rho_a)}{dp} dp} \quad (13)$$

Equations 10 and 13 may be used for estimating gas permeability and porosity, according to one or more example embodiments of the disclosure.

As illustrated previously, for an infinite long shale column with a uniform initial pore gas pressure, the porosity and permeability can be estimated as a function of pore gas pressure using Equations 10 and 13 from measurement of M(t) and p(λ), which are obtained under a constant pressure at the column inlet. It should be noted, however, that the gas compressibility and adsorption parameter, which are functions of pore gas pressure in these equations, may be independently determined or estimated from other tests or existing literature. The adsorption parameter may not be involved if gas used for a test is non-reactive.

The test method is consistent with initial and boundary conditions used to obtain Equations 10 and 13. M(t) and p(λ) can be effectively and reliably measured from a test run. Initially, shale sample 30 with a confining stress has a uniform gas pore-pressure $p_i$. The sample 30 is long enough, for example, 4 inches in length, such that it can be treated as infinitely long for a certain period of test time. The upstream gas reservoir of the shale sample 30 may then be coupled to inlet pump 16 with precise pressure and flowrate controls. The upstream pressure of the core sample 30 may be maintained as a constant $p_o$ by the inlet pump 16. The pressure range between $p_i$ and $p_0$ covers the range of practical interest or the range in which the pressure dependence is important. Cumulative gas mass flow rate into the column inlet, M(t), may be monitored. The pore gas pressure may be measured as a function of time at a given location of shale column. The monitoring locations can be set to any location except at the two ends. In one embodiment, measurement can be taken about 1 inch from the column inlet. From the transformation given in Equation 6, p(λ) can be obtained from the pressure measurements. The pressure at outlet of the sample 30 is measured to monitor pore gas pressure breakthrough. Pressure breakthrough is considered to occur at the outlet when pressure increases by about 0.1 psi. It should be noted, however, that after pressure breakthrough, the boundary effect from the downstream may be propagated to the measurement point. After time ($t_c$), the length of sample 30 cannot be treated as infinite anymore. Thus, only pressure data before time ($t_c$) can be used to calculate p(λ).

The time $t_c$ can be estimated using Equation 14 as follows:

$$t_c = t_b \left[ 1 + \left( \frac{L_b}{L} \right)^2 \right] \quad (14)$$

where $t_b$ is the time of the pressure breakthrough at the outlet of sample 30, L is the length of shale sample 30, and $L_b$ is the distance between a pressure measurement location and column outlet. The previous equation may be obtained by assuming D(p) in Equation 9 to be constant. In this case, the travel distance of the diffusion front resulting from the outlet disturbance may be proportional to the square root of the time since the pressure breaks through at the outlet.

Figure 5:
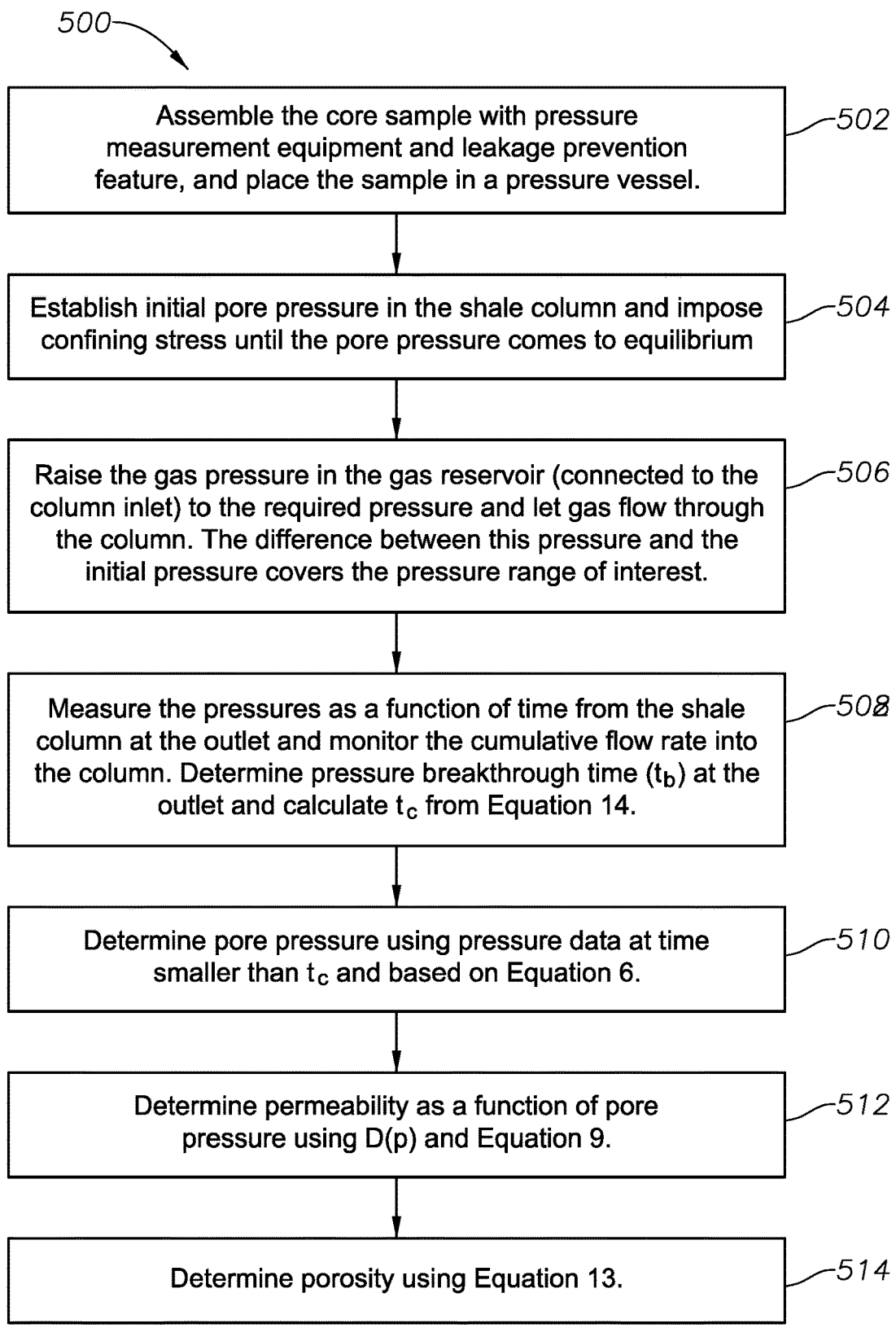
FIG. 5 shows a flow chart illustrating example operations in a method for determining permeability and porosity of a subsurface formation, according to one example embodiment of the disclosure.

Example Method for Determining Permeability and Porosity of a Subsurface Formation Turning now to FIG. 5, illustrated is a flow chart showing example operations in a method 500 for determining permeability and porosity of a subsurface formation, according to one example embodiment of the disclosure. The method uses only one pressure measurement location between the inlet and the outlet of a shale column. However, this is only for illustration purposes, and the method 500 may include pressure measurement at multiple locations along the length of the shale column. While the theory requires only one location to make the pressure measurements as a function of time, pore gas pressures at two or more locations may be measured for reasons like achieving better resolution for p(λ). It should be noted, however, that p(λ) can be constructed with pressure measurements at different locations. At each measurement location, a small hole with a diameter of 1/16" or less and with a depth to about the center of the shale column 30 may be drilled such that shale pore gas pressure can be measured reliably without causing any disturbance to the gas flow along the column.

At operation 502, the core sample may be assembled with pressure measurement equipment and leakage prevention feature, and the sample is placed in a pressure vessel, as illustrated in FIG. 1, for example. At operation 504, an initial pore gas pressure may be established in the shale column and confining stress may be imposed until the pore gas pressure achieves equilibrium. At operation 506, the pore gas pressure in the gas reservoir connected to the column inlet may be raised to the required pressure so that gas may flow through the column. The difference ($p_o - p_i$) between this pressure and the initial pressure covers the pressure range of interest. At operation 508, the pressures may be measured as a function of time from the shale column and at the outlet and monitor the cumulative flow rate into the column. At this point, the pressure breakthrough time ($t_b$) at the outlet may be determined and $t_c$ can be calculated using Equation 14 as follows:

$$t_c = t_b \left[ 1 + \left( \frac{L_b}{L} \right)^2 \right]$$

At operation 510, p(λ) may be determined using pressure data at time smaller than $t_c$ and based on Equation 6 as follows:

$$\lambda = x t^{-1/2}$$

At operation 512, D(p) may be determined based on Equation 10 and using p(λ) obtained from operation 510 as follows:

$$D(p) = -\frac{\int_{p_i}^{p} \frac{\lambda}{2} \frac{dm}{dp} dp}{\frac{dp}{d\lambda}}$$

In Equation 10, the derivative dp/dλ can be estimated from dp/dt:

$$\frac{dp}{d\lambda} = -\frac{dp}{dt} \frac{2t^{3/2}}{x} \quad (15)$$

It may be more convenient to estimate dp/dt because pressure is directly measured at location x as a function of t. The values of dp/dt can be estimated using the finite difference method with time interval of 1 second or less.

At operation 512, the permeability, k, can be determined as a function of pore gas pressure using D(p) and Equation 9 as follows:

$$D(p) = \frac{k\rho}{\mu}$$

At operation 514, the porosity may be determined with p(λ) obtained from operation 508 and Equation 13 as follows:

$$\phi = \frac{B - A \int_{p_i}^{p_0} \lambda \frac{d\rho_a}{dp} dp}{A \int_{p_i}^{p_0} \lambda \frac{d(\rho - \rho_a)}{dp} dp}$$

Figure 6:
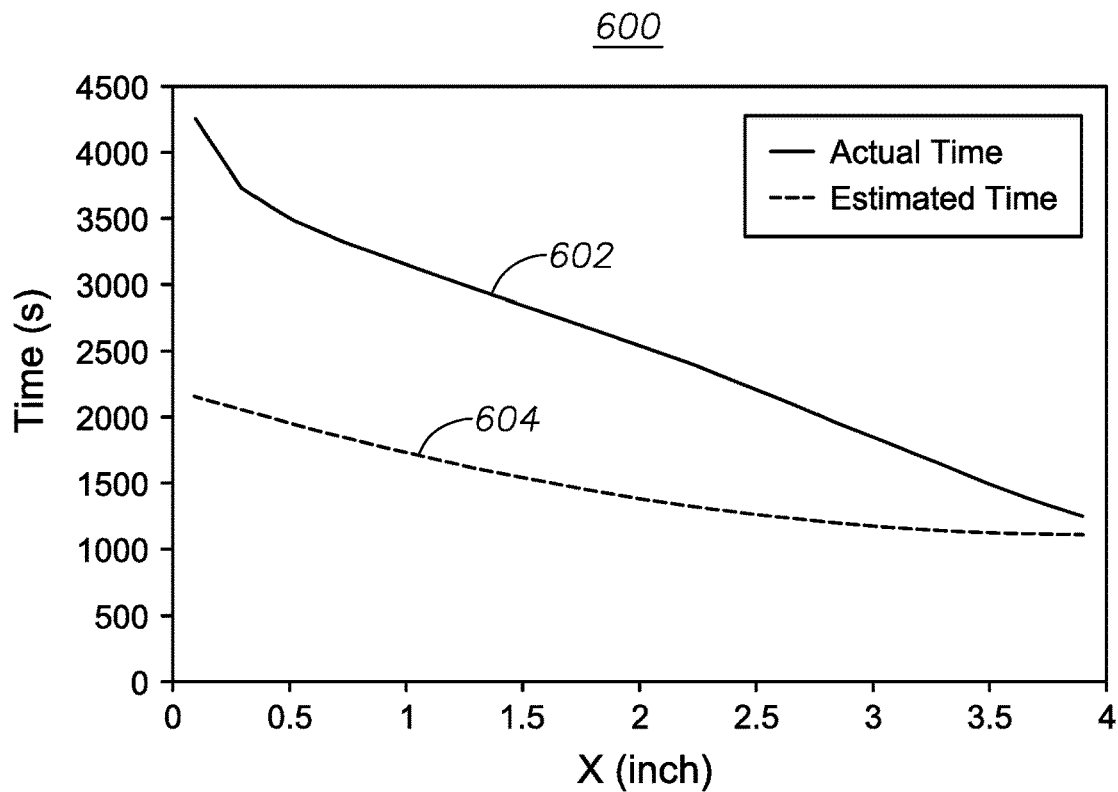
FIG. 6 shows a graphic illustrating simulated time values when the boundary effect occurs (actual time and estimated time in seconds, s) at different locations along a shale formation sample, according to one example embodiment of the disclosure.

The disclosed method is based on an analytical solution for infinitely long column. However, in the experimental data a 4" long shale column, not a finitely long column, is used, and to make sure that the infinitely long column assumption practically holds, pressure data before time $t_c$ given in Equation 14 may be used. FIG. 6 shows a graphic illustrating simulated time values 600 (based on Equation 1 and related boundary and initial conditions) when the boundary effect occurs (actual time from simulation) 602 and estimated time (from Equation 14) 604 at different locations along a shale formation sample, according to one example embodiment of the disclosure. The initial pore gas pressure in a sample may be 100 psi. Pressure at the inlet may be instantaneously raised to 1000 psi at t>0. Gas density and viscosity in Equation 1 may be treated as functions of pore gas pressure. Two columns with lengths of 4" and 12" are used in the simulations. No pore gas pressure breakthrough is observed for the long column during the test time periods; thus it can be treated as an infinitely long column. The simulated pressures at different locations for both columns are compared. The outlet boundary effect is considered to occur at a time when the pressure difference for the two columns at a location is greater than 0.1 psi. FIG. 6 shows simulated time when the boundary effect occurs 602 and the time estimated 604 from Equation 14 at different locations along the column. Clearly, estimates from Equation 14 are smaller than the simulated time values. Thus, Equation 14 can be considered to be on the conservative side. It is reliable to treat pressure data collected for t<$t_c$ as those corresponding to an infinitely long column. As a result, for a 4-inch long shale sample, the no-flow boundary effect can be minimized at X=1 inch. The valid time period for pressure measurement (0-3000 s) can cover a wide pressure range (100-750 psi) for the given example.

Figure 7:
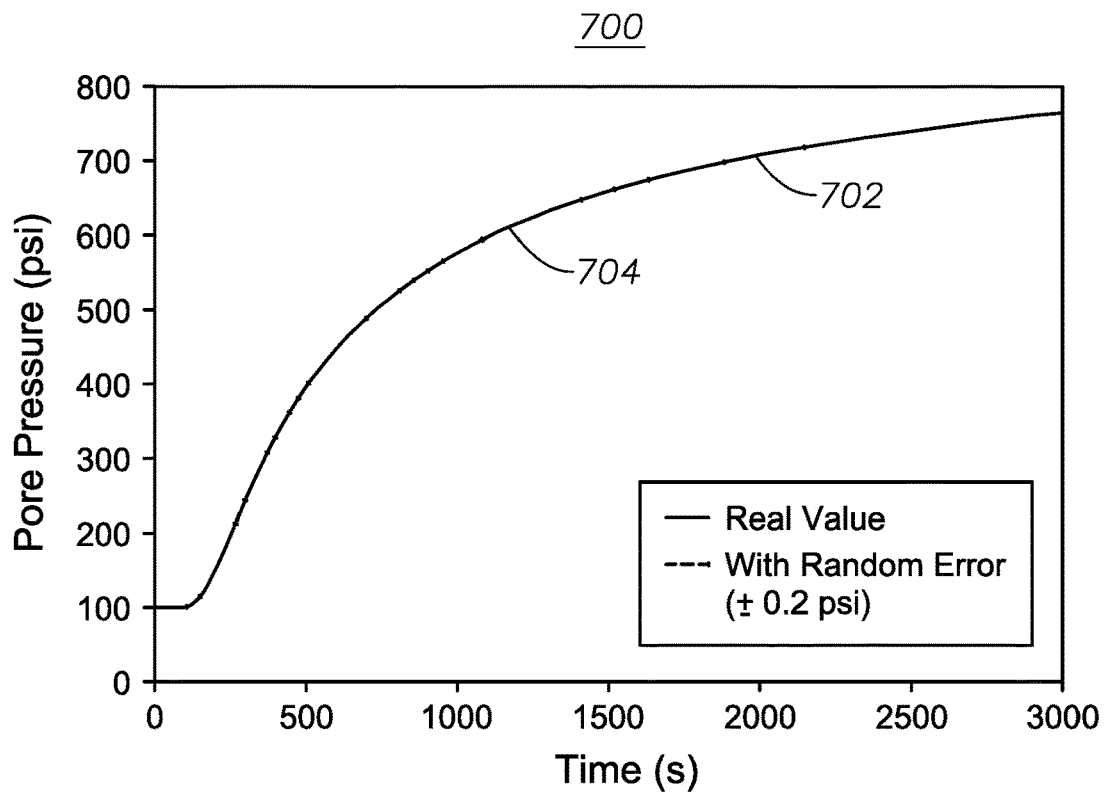
FIG. 7 shows a graphic illustrating simulated gas pore gas pressure, real value and with random error of +/−0.2 psi (pounds per square inch), as a function of time (in seconds, s) at the core location about one inch away from the inlet, according to one example embodiment of the disclosure.

Numerical experiments are also conducted to check if the test procedure gives the "true" pressure-dependency of shale gas permeability. In a numerical experiment, the "true" permeability is that used as model input. Observed pressure data from the location about 1" away from the inlet are used and random errors with magnitude of 0.2 psi are added to the simulated pressures to consider the pressure measurement errors. FIG. 7 shows a graphic illustrating simulated gas pore gas pressure 700, real value 702 and with random error of +/−0.2 psi 704, as a function of time at the core location about one inch away from the inlet, according to one example embodiment of the disclosure. The addition of random error does not make considerable difference in the pressure distribution because pressure measurement error is generally small.

As indicated by the line 602 in FIG. 6, the time when the no-flow boundary affects the pressure response in upstream locations increases with the distance to the no-flow boundary. So in order to ensure enough time for valid measurements, the pressure gauge should be put in a reasonable distance away from the boundary. However, at the same time, the pressure gauge should not be too close to the inlet because the pressure response there increases from $p_i$ to $p_o$ too fast. In the present method, the measurement location is at X=1 inch.

While doing the actual measurements, an estimated time for valid measurements can be calculated using Equation 14. Line 604 (calculated from Equation 14) in FIG. 6 indicates that it is a conservative estimation and thus can be safely used in practice.

Figure 8:
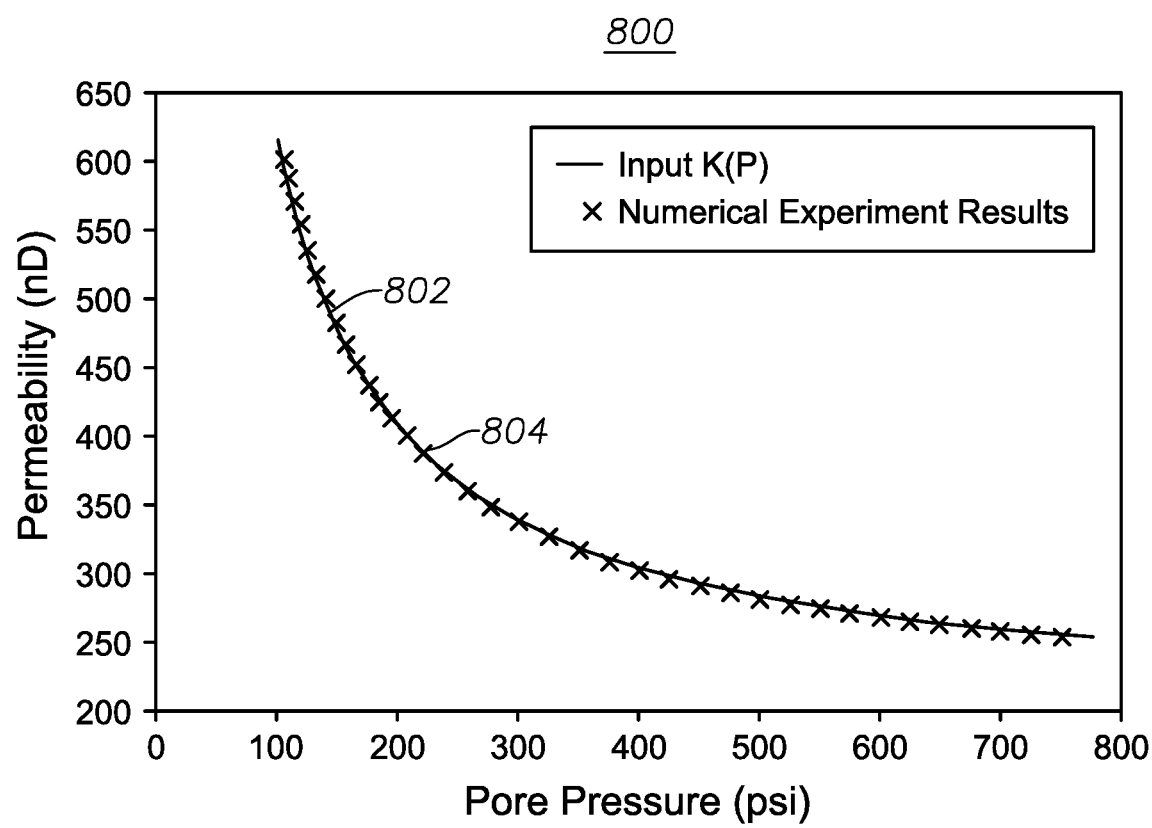
FIG. 8 shows a graphic illustrating comparison between the true permeability as a function of pore gas pressure and the permeability from numerical experiment results, according to one example embodiment of the disclosure.

FIG. 8 shows a graphic illustrating comparison between the true permeability as a function of pore gas pressure and the permeability from numerical experiment results, according to one example embodiment of the disclosure. As shown in the graph 800 in FIG. 8, results 804 based on the laboratory test procedure disclosed with input k(p) and pressure data obtained from numerical experiments are almost identical to the "true" values 802 (or input k(p)), indicating that the proposed procedure is accurate and reliable. It can be observed that they are highly consistent with each other, which also means that the recorded pressure response is very close to that in the theoretical model and the boundary effect is minimized at location X=1 inch.

Computer Readable Medium

Figure 9:
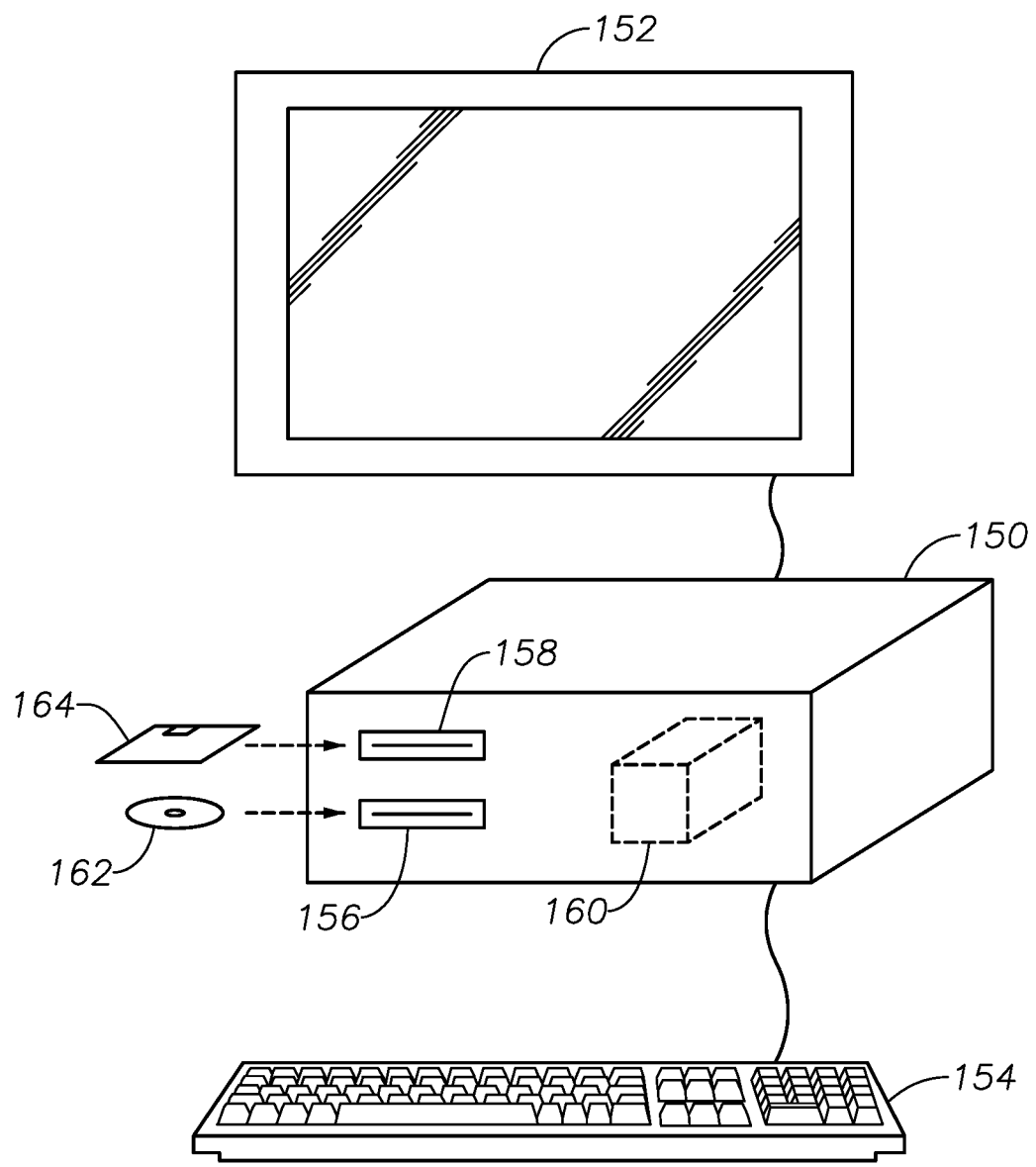
FIG. 9 shows a special purpose computer and various forms of computer readable media for determining the impact of Knudsen diffusion and mechanical deformation on the permeability a subsurface formation, according to some example embodiments of the disclosure.

Another example embodiment is a special purpose computer configured to execute specific computer instructions in a computer program stored in computer readable media. Referring to FIG. 9, the foregoing process as explained with reference to FIGS. 1-8 can be embodied in computer-readable code. The code can be stored on, for example, a computer readable medium, such as a floppy disk 164 which may be read by a disk drive 158, CD-ROM 162, which may be read by a disk drive 156, or a magnetic (or other type) hard drive 160 forming part of a general purpose programmable computer. The computer, as known in the art, includes a central processing unit 150, a user input device such as a keyboard 154 and a user display 152 such as a flat panel display or cathode ray tube display. According to this aspect, the computer readable medium includes logic operable to cause the computer to execute acts as set forth previously and explained with respect to the previous figures. The non-transitory computer-readable medium having computer executable instructions cause a computer to perform the operations of reading a measurement of a first pore gas pressure, $p_i$, inside a sample assembly 300 comprising a sample of a subsurface formation, gas, and a pressure gauge. The instructions also include reading a measurement of a second pore gas pressure, $p_o$, applied to the inlet of a sample, where the second pore gas pressure is greater than the first pore gas pressure. The instructions also include reading a measurement of a third pore gas pressure, p, at location x at time t in the sample, and determining a total gas mass per unit volume of the subsurface formation, m. The instructions also include determining a permeability of the subsurface formation, k, based at least in part on the first pore gas pressure, the second pore gas pressure, the third pore gas pressure, and the gas density.

The computer executable instructions further cause the computer to perform the operation of determining the transport parameter of the subsurface formation, D(p), using a first formula:

$$D(p) = -\frac{\int_{p_i}^{p} \frac{\lambda}{2} \frac{dm}{dp} dp}{\frac{dp}{d\lambda}}$$

where $p_i$ is the first pore gas pressure inside the sample in assembly 300 before the second pore gas pressure $p_o$ is applied, p is the third pore gas pressure at location x at time t, m is the total gas mass per unit volume of the subsurface formation, and $\lambda$ is an independent variable calculated using the formula $xt^{-1/2}$. Then permeability can be determined from D(p) using Equation 9.

The computer executable instructions further cause the computer to perform the operation of determining the total gas mass per unit volume of the subsurface formation, m, using a second formula:

$$m = \phi\rho + (1-\phi)\rho_a$$

where $\phi$ is porosity of the subsurface formation, $\rho$ is gas density of the natural gas, and $\rho_a$ is adsorbed gas mass per unit volume of the subsurface formation.

The computer executable instructions further cause the computer to perform the operation of determining the porosity $\phi$ of the subsurface formation using a third formula:

$$\phi = \frac{B - A\int_{p_i}^{p_0} \lambda \frac{d\rho_a}{dp} dp}{A\int_{p_i}^{p_0} \lambda \frac{d(\rho - \rho_a)}{dp} dp}$$

where A is a cross-sectional area of the sample, and B is a slope of a curve of the cumulative gas flow into the sample at x=0 versus $t^{1/2}$.

The computer executable instructions further cause the computer to perform the operation of determining the slope of the curve, B, using a fourth formula:

$$B = A\int_{p_i}^{p_0} \lambda \frac{dm}{dp} dp$$

Methods according to the present disclosure provide improved estimates of permeability as a function of pore gas pressure and porosity of subsurface rock formations. Analytical models used to measure pressure-dependent gas permeability of shale are disclosed. Example methods and systems to measure shale gas permeability as a function of pore gas pressure are disclosed. The advantages of this approach over the currently available ones include that it measures pressure-dependent gas permeability more efficiently using a single test run and without any presumption regarding a parametric relationship between gas permeability and pressure. In addition, the disclosed embodiments consider the impact of mechanical deformation. Therefore, the disclosed methods and systems include a workflow using two-or-more-step permeability tests, which can measure the impacts of Knudsen diffusion and the mechanical deformation of the rock on permeability, respectively. In addition, example embodiments also allow for estimating shale porosity from the related measurements.

Figure 10:
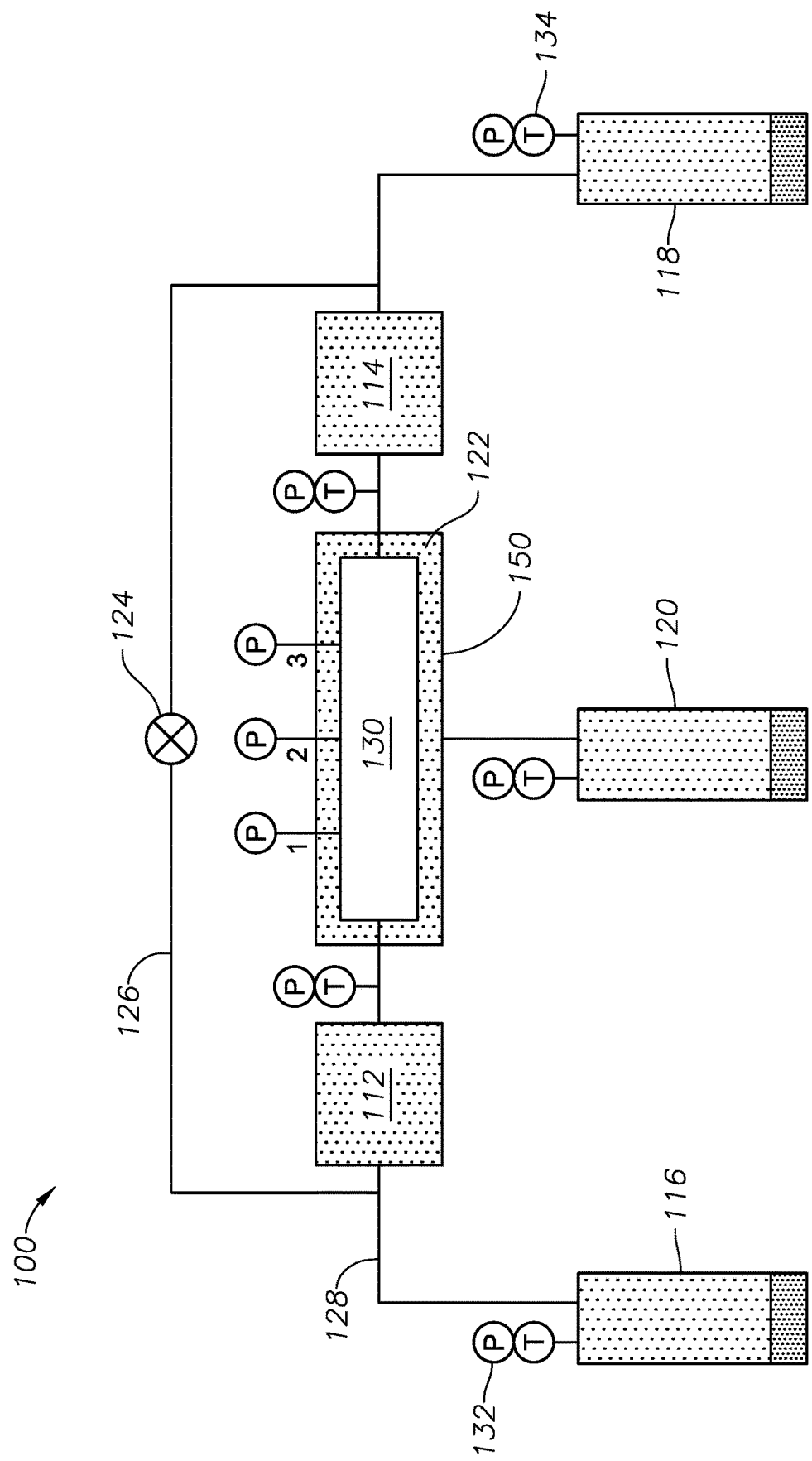
FIG. 10 illustrates an example system for determining the impact of Knudsen diffusion and mechanical deformation on the permeability a subsurface formation, according to one example embodiment of the disclosure.

FIG. 10 illustrates an example system 100 for determining the impact of Knudsen diffusion and mechanical deformation on the permeability a subsurface formation, according to one example embodiment of the disclosure. System 100 includes sample 130, such as a shale sample, a limestone sample, or a sandstone sample, in the form of a cylinder or column that may be extracted from the subsurface for determining characteristics of the formation. The sample 130 is placed in a pressure vessel 150 that may contain a confining fluid 122, such as gas, a water-based fluid, or an oil-based fluid. The pressure vessel 150 is coupled to pumps 116, 118 through pressure lines 128 that provide the confining pressure to the sample 130.

System 100 includes an inlet pump 116 configured to pump fluid from a first gas tank 112, for example an upstream reservoir, into sample 130. The system also includes an outlet pump 118 configured to pump fluid from a second gas tank 114, for example a downstream reservoir, into sample 130. Both pumps may include one or more pressure sensors 132, temperatures sensors 134, and flowrate sensors to measure and control the pressure inside the core sample assembly. Pressure vessel 150 may be equipped with a hydraulic pump 120, which may also be referred to as the confining pump, that may pump the confining fluid 122 into pressure vessel 150. The pressure vessel 150 may include an apparatus that monitors and regulates the pressure within the pressure vessel 150. Temperature gauges 134 and pressure gauges 132 are coupled to the pressure lines 128 and the pumps 116, 118, 120. Both gauges may include high accuracy transducers (with a typical accuracy of 0.01%) to measure temperature and pressure, respectively, in real-time. The inlet to the core sample assembly may be diverted at one or more points using bypass valves 124 and an outlet pipe 126 in order to regulate the pore gas pressure (for example, the establishment of the initial pore pressure) in sample 130 which is placed in the pressure vessel 150.

Figure 11:
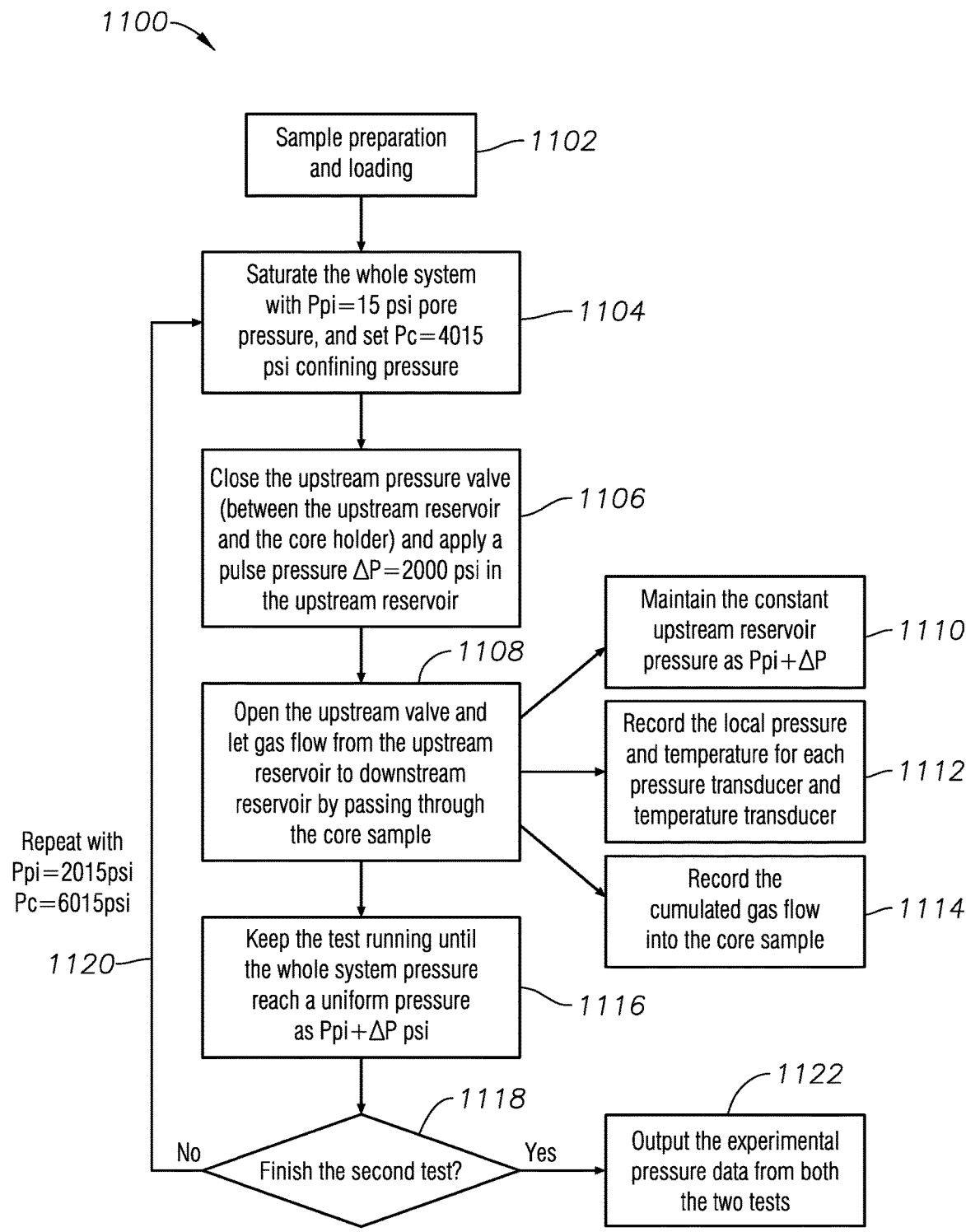
FIG. 11 shows a flow chart illustrating example operations in a method for determining the impact of Knudsen diffusion and mechanical deformation on the permeability a subsurface formation, according to one example embodiment of the disclosure.

FIG. 11 shows a flow chart illustrating example operations in a method 1100 for determining the impact of Knudsen diffusion and mechanical deformation on the permeability a subsurface formation, according to one example embodiment of the disclosure. At step 1102, a cylindrical core plug sample 130 is prepared and assembled in the vessel 150 by connecting three side ports 1, 2, 3, along a longitude direction of the sample 130. At step 1104, the pressure-dependent permeability test is initiated by saturating or equilibrating the first gas tank 112, second gas tank 114, and the vessel 150 to reach a uniform initial pore pressure, $P_{pi}$, and provide a confining stress, $P_c$. In one example, $P_{pi}$=15 psi for pore pressure and $P_c$=4015 psi for confining stress. At step 1106, an upstream pressure valve between the first gas tank 112 and the vessel 150 is closed, and a pressure increase, $\Delta P$ (for example $\Delta P$=2000 psi), is applied in the first gas tank 112. At step 1110, the pressure in the first gas tank, $P_{up}$, will be equal to $P_{pi}+\Delta P$ (for example $P_{pi}+\Delta P$=2015 psi). At step 1108, the first gas tank's valve is opened and the gas is allowed to flow from the first gas tank 112 to the second gas tank 114 via the core sample 130. During this time the pressure in the first gas tank 112 is kept constant (for example, $P_{up}$=2015 psi), and the confining stress and laboratory temperature (for example, $P_c$=4015 psi, and T=50° C.) are maintained to be constant as well. At step 1112, the local pressure and temperature from each of the pressure sensors and temperature sensors is recorded. Meanwhile, the cumulated gas flow into the core sample and the local pressure with respect to each transducer are recorded at step 1114. At step 1116, the test is run until the system reaches a uniform pressure (all pressure gauges readings are the same $P_{up}$ (for example, 2015 psi)).

At step 1118, the system checks if a second test is to be conducted. If yes, then at step 1120 a second test is conducted by repeating the disclosed steps with different initial pore pressure and confining stress (for example, $P_{pi}$=2015 psi pore pressure, $P_c$=6015 psi confining stress). With this presetting, the effective stress range, that is the difference between confining stress and pore pressure is same as the one in the first test. After the second pressure-dependent permeability test is completed, at step 1122, the experimental data from the tests are outputted to a special purpose computer for further data analysis.

In one example embodiment, the tests are conducted under isothermal conditions so that all the related parameters are considered as a function of pressure. For example, if $P_{pi}$=15 psi and $P_c$=4015 psi for the first test, and $P_{pi}$=2015 psi and $P_c$=6015 psi for the second test, then the effective stress range is the same for these two tests, that is 4000 psi. While, for the first test, the pore pressure is increased from 15 psi to 2015 psi, and for the second test the pore pressure is increased from 2015 to 4015 psi. In the first test, the Knudsen diffusion and the rock mechanic deformation both exist. In the second test, since the pore pressure is in the range from 2015 psi to 4015 psi, the Knudsen diffusion is negligible and only the rock mechanic deformation exists. Therefore, by comparing the results of these two tests, the impacts of the Knudsen diffusion and rock mechanic deformation on the rock matrix permeability can be separated and determined.

Figure 12:
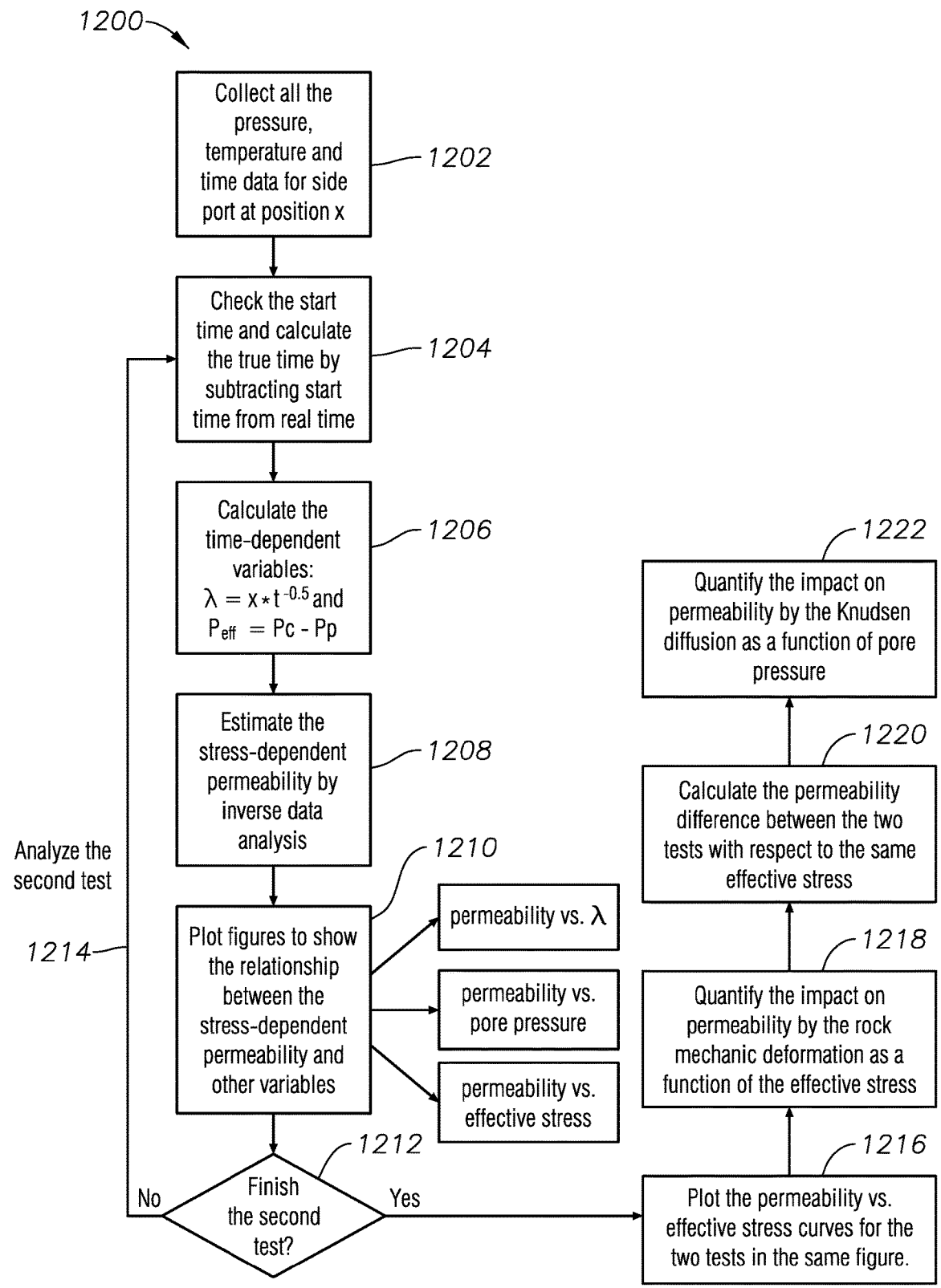
FIG. 12 shows a flow chart illustrating example operations in a method for determining the impact of Knudsen diffusion and mechanical deformation on the permeability a subsurface formation, according to one example embodiment of the disclosure.

FIG. 12 shows a flow chart illustrating example operations in a method 1200 for determining the impact of Knudsen diffusion and mechanical deformation on the permeability a subsurface formation, according to one example embodiment of the disclosure. At step 1202, the starting time is determined as gas starts to flow from the upstream reservoir to the downstream reservoir by passing through the core sample. At step 1204, the true measurement of time is calculated by subtracting the starting time from the real time. At step 1206, the distance between the gas inlet to the position of each side port as 'x' is determined, and λ is calculated for each side ports using Eq. 6. At step 1208, the pressure-dependent permeability is determined by applying inverse data analysis on experimental data. At step 1210, graphs are plotted to show the relationship between the pressure-dependent permeability and other parameters, including permeability versus λ, permeability versus pore pressure, and permeability versus effective stress.

At step 1212, the system checks to see if the second test is completed. If the second test is completed, then at step 1214 the system analyses the results from the second test by repeating the disclosed steps 1202 to 1212. At step 1216, the permeability versus effective stress curves are plotted in the same figure for the two tests with different range of pore pressure. At step 1218, the impact of rock mechanic deformation on the rock matrix permeability is determined using the results of the second test with the higher pore pressure range (for example the pore pressure range is between 2000 to 4000 psi during which the Knudsen diffusion is negligible). At step 1220, the impact of the Knudsen diffusion on the rock matrix permeability is determined by subtracting the permeability value of the higher pore pressure test (for example, 2000 to 4000 psi) from the one of the lower pore pressure test (for example, 1000 psi or lower) for a given effective stress. At step 1222, the impact of rock mechanic deformation is determined by finding the relationship between the effective stress and the permeability at higher pore pressure, at which Knudsen diffusion is negligible, and the impact of the Knudsen diffusion is determined by finding the relationship between the pore pressure and the permeability at lower pore pressure.

Figure 13:
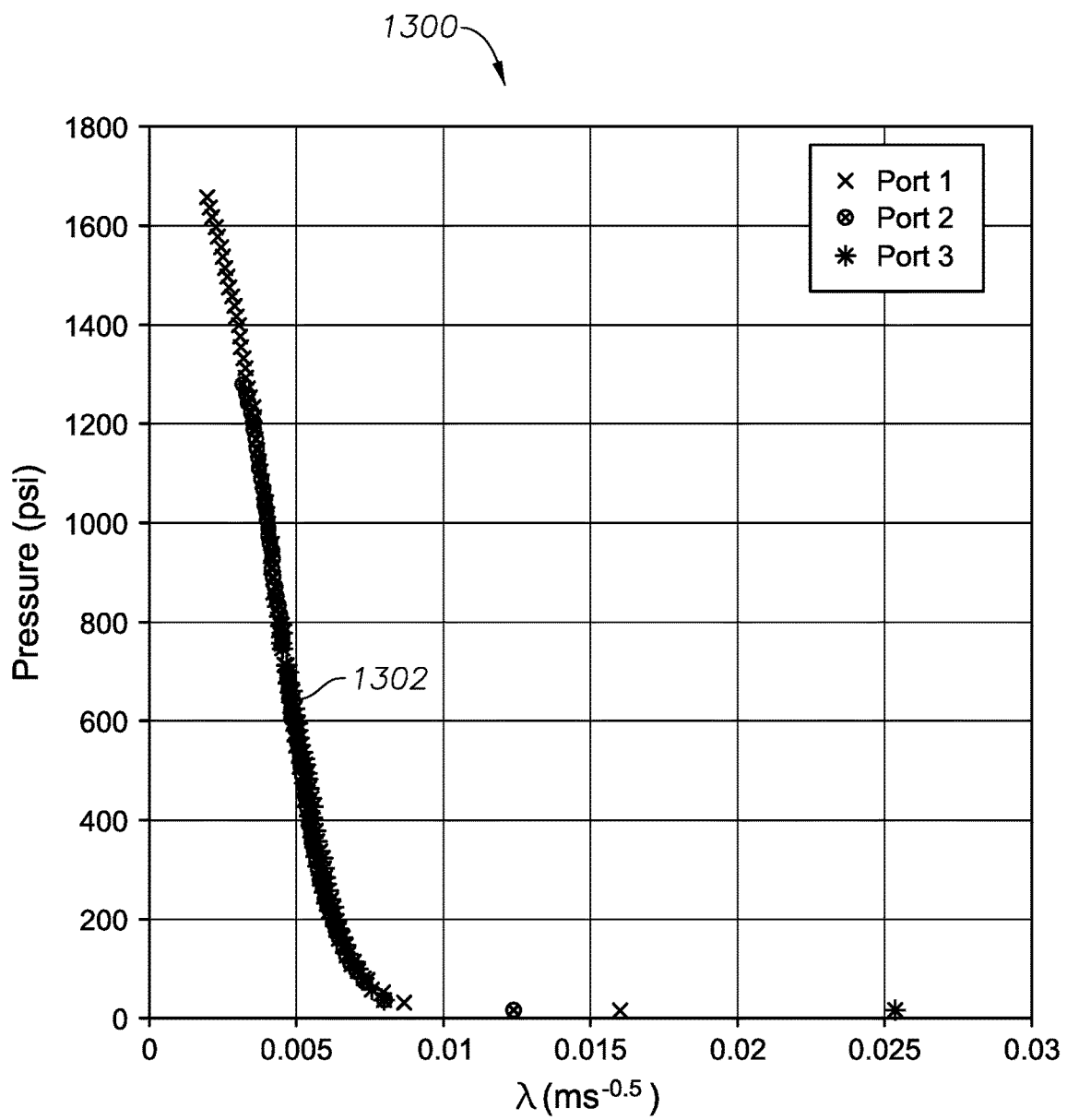
FIG. 13 is an illustrative graph showing pore pressure (psi) versus confining stress ($\lambda$ expressed in meter per second square root) obtained from experiment results, according to one example embodiment of the disclosure.

FIG. 13 is an illustrative graph 1300 showing pore pressure (psi) versus confining stress (λ) obtained from experimental results, according to one example embodiment of the disclosure. Line 1302 shows the first stress-dependent permeability test results with low pore pressure with respect to three side ports, respectively. The λ value is calculated using Eq. 11 and the measurement time and three side ports distances from the inlet of core sample, respectively.

Figure 14:
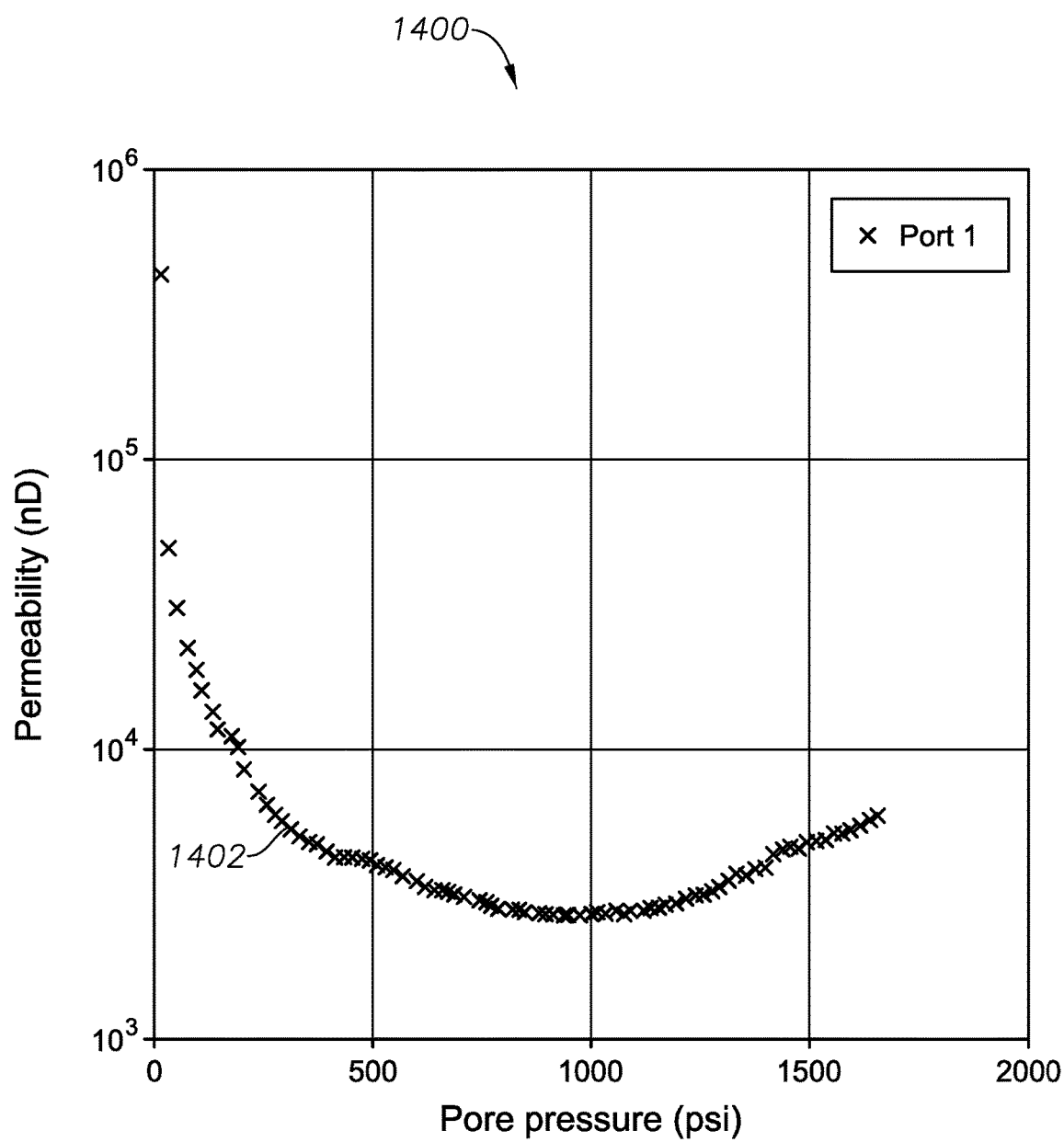
FIG. 14 is an illustrative graph showing pore pressure (psi) versus permeability (nano Darcy, nD) of the subsurface formation obtained from experiment results, according to one example embodiment of the disclosure.

FIG. 14 is an illustrative graph 1400 showing pore pressure (psi) versus permeability (nD) of the subsurface formation obtained from experimental results, according to one example embodiment of the disclosure. In this permeability curve 1402, it can be observed that with the increase of pore pressure from about 100 psi to around 1000 psi, the permeability decreases. In the other words, when the pore pressure is lower than 1000 psi, the impact of Knudsen diffusion on permeability is much greater than rock mechanic deformation, leading to the decrease of permeability. When the pore pressure is greater than 1000 psi, permeability increases with the increase of the pore pressure. Therefore, it can be explained that the impact of the Knudsen diffusion is smaller than rock mechanic deformation above 1000 psi pore pressure. In order to separate the impact of Knudsen diffusion and rock mechanic deformation, a second stress-dependent permeability test with high pore pressure range needs is conducted.

Therefore, example methods and systems disclosed here include conducting two pressure-dependent permeability tests having the same range of effective stress (which equals to confining stress minus pore pressure) but two different values of pore pressure. For the test with the higher pore pressure, the permeability is only impacted by the mechanical deformation of the rock, while for the one with lower pore pressure the permeability is impacted by both mechanical deformation of the rock and the Knudsen diffusion. By using the same range of effective stress, the contribution from the mechanical deformation of the rock should be the same. Therefore, by subtracting the permeability with higher pore pressure from the one with lower pore pressure, the impact of Knudsen diffusion and the mechanical deformation of the rock can be determined.

Although the technology here has been described with reference to particular embodiments, it is to be understood that these embodiments are merely illustrative of the principles and applications of the present technology. It is therefore to be understood that numerous modifications may be made to the illustrative embodiments and that other arrangements may be devised without departing from the spirit and scope of the present technology as defined by the appended claims.

The invention claimed is:

1. A transient flow method for determining gas permeability of a subsurface formation, comprising:
   acquiring a sample of the subsurface formation;
   positioning the sample in a pressure vessel comprising a fluid and a pressure gauge and applying a constant confining pressure, $P_c(1)$;
   running a first test by equilibrating the sample at a predetermined first pore gas pressure, $p_i$;

applying a predetermined constant second gas pressure, $p_o$, to an inlet of the sample, the second gas pressure being greater than the first pore gas pressure;

measuring a third pore gas pressure, p, as a function of time, t, at a plurality of locations along the axis of the sample in the pressure vessel;

in a computer, determining a gas density or total gas mass per unit volume of the subsurface formation, m; and in the computer, determining the gas permeability of the subsurface formation as a function of pore pressure, k(p), based at least in part on the first pore gas pressure, the second gas pressure, the third pore gas pressure as a function of time, and the gas density as a function of pore pressure.

2. The method according to claim 1, further comprising:
determining a transport parameter of the subsurface formation, D(p), using a first formula:

$$D(p) = -\frac{\int_{p_i}^{p} \frac{\lambda}{2} \frac{dm}{dp} dp}{\frac{dp}{d\lambda}}$$

where $\lambda$ is an independent variable calculated using the formula $k=xt^{-1/2}$; and determining gas permeability k of the subsurface formation from D(p) using $$D(p) = \frac{k\rho}{\mu}$$

where $\mu$ stands for gas viscosity, and $\rho$ for gas density.

3. The method according to claim 2, further comprising:
determining the total gas mass per unit volume of the subsurface formation, m, using a second formula:

$$m=\phi\rho+(1-\phi)\rho_a$$

where $\phi$ is porosity of the subsurface formation, $\rho$ is gas density of the gas, and $\rho_a$ is adsorbed gas mass per unit volume of the subsurface formation.

4. The method according to claim 3, further comprising:
determining the porosity $\phi$ of the subsurface formation using a third formula:

$$\phi = \frac{B - A\int_{p_i}^{p_0} \lambda \frac{d\rho_a}{dp} dp}{A\int_{p_i}^{p_0} \lambda \frac{d(\rho-\rho_a)}{dp} dp}$$

where A is a cross-sectional area of the sample, and B is a slope of a curve of the cumulative gas flow into the sample at x=0 versus $t^{1/2}$.

5. The method according to claim 4, further comprising:
determining the slope of the curve, B, using a fourth formula:

$$B = A\int_{p_i}^{p_0} \lambda \frac{dm}{dp} dp$$

6. The method according to claim 1, wherein the subsurface formation comprises at least one of shale, limestone, and sandstone.

7. The method according to claim 1, further comprising:
running a second test with a fourth pore pressure and a fifth pressure with a second constant confining pressure, $P_c(2)$, wherein the fourth pore pressure is greater than the first pore pressure, the fifth pressure is greater than the second pressure, and the second constant confining pressure $P_c(2)$, is greater than the first constant confining pressure $P_c(1)$;

generating a graph plotting permeability versus effective stress for the first test and the second test;

determining impact of mechanical deformation of rock on permeability as a function of the effective stress;

determining the difference between permeability values obtained from the first test and the second test with respect to the effective stress; and determining impact of Knudsen diffusion on permeability as a function of the pore pressure.

8. A non-transitory computer-readable medium having computer executable instructions that cause a computer to perform the operations of:

reading a measurement of a first pore gas pressure, $p_i$, of a gas after equilibrating the sample in a pressure vessel comprising a fluid and a pressure gauge that reads the constant confining pressure $P_c(1)$ after it is applied;

reading a measurement of a predetermined constant second gas pressure, $p_o$, applied to an inlet of the sample, the second gas pressure being greater than the first pore gas pressure;

reading a measurement of a third pore gas pressure, p, at time, t, at a plurality of locations along the axis of the sample;

determining a total gas mass per unit volume of the subsurface formation, m; and determining gas permeability of the subsurface formation as a function of pore pressure, k(p), based at least in part on the first pore gas pressure, the second pressure, the third pore gas pressure, and the gas density as a function of pore pressure.

9. The non-transitory computer-readable medium of claim 8, wherein the computer executable instructions further cause the computer to perform the operation of:

determining a transport parameter of the subsurface formation, D(p), using a first formula:

$$D(p) = -\frac{\int_{p_i}^{p} \frac{\lambda}{2} \frac{dm}{dp} dp}{\frac{dp}{d\lambda}}$$

where $\lambda$ is an independent variable calculated using the formula $xt^{-1/2}$; and determining gas permeability, k, from D(p) using $$D(p) = \frac{k\rho}{\mu}$$

where $\mu$ stands for gas viscosity, and $\rho$ for gas density.

10. The non-transitory computer-readable medium of claim 9, wherein the computer executable instructions further cause the computer to perform the operation of:

determining the total gas mass per unit volume of the subsurface formation, m, using a second formula:

$$m=\phi\rho+(1-\phi)\rho_a$$

where $\phi$ is porosity of the subsurface formation, $\rho$ is gas density of the gas, and $\rho_a$ is adsorbed gas mass per unit volume of the subsurface formation.

11. The non-transitory computer-readable medium of claim 10, wherein the computer executable instructions further cause the computer to perform the operation of:

determining the porosity $\phi$ of the subsurface formation using a third formula:

$$\phi = \frac{B - A\int_{p_i}^{p_0} \lambda \frac{d\rho_a}{dp} dp}{A\int_{p_i}^{p_0} \lambda \frac{d(\rho - \rho_a)}{dp} dp}$$

where A is a cross-sectional area of the sample, and B is a slope of a curve of the cumulative gas flow into the sample at x=0 versus $t^{1/2}$.

12. The non-transitory computer-readable medium of claim 11, wherein the computer executable instructions further cause the computer to perform the operation of:

determining the slope of the curve, B, using a fourth formula:

$$B = A\int_{p_i}^{p_0} \lambda \frac{dm}{dp} dp$$

13. The non-transitory computer-readable medium of claim 8, wherein the subsurface formation comprises at least one of shale, limestone, and sandstone.

14. The non-transitory computer-readable medium of claim 8, further comprising reading a measurement of a fourth pore gas pressure, of a gas after equilibrating the sample in a pressure vessel comprising a fluid and a pressure gauge that reads the constant confining pressure $P_c$ (2) after it is applied;

reading a measurement of a predetermined constant fifth gas pressure, applied to an inlet of the sample, the fifth gas pressure being greater than the fourth pore gas pressure; and reading a measurement of pore gas pressure, p, at time, t, at a plurality of locations along the axis of the sample.

15. The non-transitory computer-readable medium of claim 8, wherein the computer executable instructions further cause the computer to perform the operation of:

generating a graph plotting permeability versus effective stress for the first test and the second test;

determining impact of mechanical deformation of rock on permeability as a function of the effective stress;

determining the difference between permeability values obtained from the first test and the second test with respect to the effective stress; and determining impact of Knudsen diffusion on permeability as a function of the pore pressure.

* * * * *